United States Patent [19]

Smith et al.

[11] Patent Number: 5,175,246

[45] Date of Patent: Dec. 29, 1992

[54] MEDICAL GRADE ADHESIVES AND THEIR PREPARATION

[75] Inventors: Daniel J. Smith, Stow; Oscar C. Mascarenhas, Akron, both of Ohio

[73] Assignee: University of Akron, The, Akron, Ohio

[21] Appl. No.: 823,856

[22] Filed: Jan. 22, 1992

[51] Int. Cl.$^5$ .................... C08G 59/00; C08G 59/22; C08G 59/26
[52] U.S. Cl. .................. 528/405; 528/407; 523/111
[58] Field of Search ............... 523/111; 528/405, 407

[56] References Cited

U.S. PATENT DOCUMENTS

| | | | |
|---|---|---|---|
| 4,231,369 | 11/1980 | Sorenson et al. | 128/283 |
| 4,593,053 | 6/1986 | Jeune et al. | 523/111 |
| 4,685,990 | 8/1987 | Ferguson | 156/253 |
| 4,778,825 | 10/1988 | Smith et al. | 514/669 |
| 4,781,921 | 11/1988 | Smith et al. | 424/81 |
| 4,937,269 | 6/1990 | Smith et al. | 514/669 |

FOREIGN PATENT DOCUMENTS 1088992 10/1967 United Kingdom.
2198441 6/1988 United Kingdom.

OTHER PUBLICATIONS

Alvarez, O. M. et al., The Effect of Occlusive Dressing on Collagen Synthesis and Reepithelialization in Superficial Wound, J. Surg. Res., 35: 142-148 (1983).

Annual Book of ASTM Standards, Standard Test Method for Peel Adhesion of Pressure Sensitive Tape at 180° Angle [metric]. D330M-87.

Freshney, R. I., Culture of Animal Cells: A Manual of Basic Techniques., 2nd Ed., 1987, published by Alan R. Liss, Inc., New York, N.Y.; pp 74 and 75.

Park, G. B., Burn Wound Covering—A Review, Biomat. Med. Devices Artif. Organs., 6: 1-35 (1978).

Pokharna, H. K. et al., Journal of Bioactive and Compatible Polymers, 5, 42-52 (1990).

Quin, K. J. et al., Principals of Burn Dressing, Biomaterial, 6: 396-76 (1985).

Silverman, R. A. et al., Effects of Occlusive and Semiocclusive Dressing on Return of Barrier Function to Transepidermal Water Loss in Standardized Human Wounds, Journal of American Academy of Dermatology, 20, 755-60 (1989).

Smith, D. J. et al., J. Pol. Sci: Polymer Letter Edition, 23: 633-637, pp. 4, 9, 23, 44.

West, R. et al., J. Am. Chem. Soc., 90(3), 727-731 (1968).

Wheelland, R. G., The Newer Surgical Dressings and Wound Healing, Dermatological Clinics, 5(2), 393-407 (1987).

*Primary Examiner*—Paul R. Michl
*Assistant Examiner*—LaVonda R. DeWitt
*Attorney, Agent, or Firm*—Oldham, Oldham & Wilson Co.

[57] ABSTRACT

Crosslinked hydrogel polymers are made by reacting a disubstituted aliphatic diamine of the general formula (I) or (XI) as given in the specification, with one or more diepoxides having the general formula (II), also as given in the specification, and subjecting the resulting non-crosslinked polymer having repeating units of the formula III or XIII to crosslinking conditions to produce the desired crosslinked hydrogel polymer. Hydrogel polymers thus produced are highly hydrophilic with a high degree of water uptake and a high equilibrium water content. In addition, these hydrogel polymers are highly absorptive of fluids and are adhesive when applied to dry surfaces but not when applied to wet surfaces. The hydrogel polymers are useful in wound dressings.

23 Claims, 1 Drawing Sheet

MEDICAL GRADE ADHESIVES AND THEIR PREPARATION

TECHNICAL FIELD

This invention relates to novel, hydrophilic, skin-compatible, pressure sensitive adhesive gel compositions which are useful in biomedical applications including wound dressings. These compositions can be briefly described as medical grade adhesives.

BACKGROUND ART

A major effort has been directed towards the development of new synthetic wound dressings which attempt to meet the requirements in the treatment of skin wounds. Such effort is described, for example, in Park, G. B., "Burn Wound Covering-A Review", *Biomat. Med. Devices Artif. Organ.* 6; 1-35 (1978). An important class of synthetic dressings for wound repair, which is receiving increasing clinical acceptance, are occlusive dressings.

Occlusive dressings are shown to expedite reepithelialization (i.e., growth of new skin tissue) in comparison to gauze, this effect being attributed to the physical properties of the occlusive dressings, according to the Alvarez, O. M. et al, "The effect of occlusive dressing on collagen synthesis and reepithelialization in superficial wound" *J. Surg Res.*, 35: 142-148 (1983). Optimum characteristics desirable in occlusive wound dressings are: (1) adherence to non-wounded skin, (2) permeability to oxygen and water, and (3) ability to exclude bacteria, combined with a high absorptivity of fluids, according to Silverman, R. A. et al, "Effects of occlusive and semiocclusive dressings on return of barrier function to transepidermal water loss in standardized human wounds", *J. of American Academy of Dermatology*, 20, 755-760 (1989). Other authors, e.g., Quinn, K. J. et al "Principles of burn dressing", *Biomaterials*, 6: 369-376 (1985) and Park, G. B. cited supra states that the development of an adhesive that does not function as a moisture transmission barrier but is sufficiently permeable to allow absorptivity of wound exudate would be highly desirable and would also potentially have the following properties: (1) extended adhesion to wound surface (2) high absorption of wound fluids with concomitant loss of adhesive properties when in contact with a wet wound, and (3) provision of a non-cytotoxic substratum to support normal adhesion of mammalian fibroblasts and keratinocytes, and (4) complete removability of the dressing without causing any damage to the wound.

Occlusive wound dressings generally fall into one of two classes. Dressings in the first class are composed of an absorbent or non-absorbent material and an adhesive in separate layers (the adhesive constituting the outside layer) on a polymeric (e.g., polyurethane) backing. Such wound dressings are disclosed, for example, in Wheeland, R. G., "The newer surgical dressings and wound healing", *Dermatologic Clinics*, 5(2), 393-407 (1987). The second class are dressings comprising an adhesive blend, which in turn comprises an adhesive material (typically a pressure sensitive material) and a moisture absorbing material, on a polymeric film backing layer. Representative references are U.K. Patent No. 1088992 and published U.K. Patent application GB 2198441A. U.K Patent No. 088992 describes an adhesive blend which comprises a water soluble or water swellable hydrocolloid and a water insoluble viscous elastic binder, on a backing of a water-impervious material. Published U.K Patent application GB 2198441A describes a dressing of this type in which the adhesive blend comprises a pressure sensitive adhesive material (e.g., an acrylic adhesive) and an alginate, which may be either water soluble (preferred) or water insoluble. The alginate renders the pressure sensitive adhesive blend highly water absorbable. The adhesive blend or layer may also contain a medicament. The backing layer comprises a water impervious but moisture vapor transmitting continuous polymer film, e.g., polyurethane.

U.S. Pat. No. 4,593,053 to Jevne et al describes hydrophilic, skin-compatible, pressure sensitive, solid, adhesive hydrogel compositions, comprising 25-50 weight per cent (preferably about 30-40 weight percent) polyvinyl pyrrolidone (PVP), about 2-5 weight percent (preferably about 3-4 weight percent) polyvinyl alcohol (PVA), about 5-40 weight percent polar plasticizer or humectant, about 3-50 weight percent water, and optionally (depending on the application) a pharmaceutically effective amount of a desired drug or sufficient ionic species to provide conductivity to the composition. These compositions are disclosed as being useful in biomedical applications including wound dressings.

D. J. Smith et al, in *J. Polymer Sci. Polymer Letters Edition*, 23, 633-637 (1985) and in U.S. Pat. No. 4,781,921, disclose hydrophilic hydrogels which are cross linked polymers of entprol methacrylate (also known as "Quadrol" methacrylate) and entprol dimethacrylate (also known as Quadrol dimethacrylate). ["Quadrol" is a trademark [BASF] for the compound N,N',N'-tetrakis(2-hydroxypropyl)ethylenediamine].

Also disclosed are the corresponding monomers and the precursors N,N'-bis(2-hydroxypropyl)ethylenediamine and N,N'-tris(2-hydroxy propyl)ethylenediamine. The former is made by reaction of 2 mols of propylene oxide with one mol of ethylenediamine and the latter is made by reacting the former precursor with one additional mole of propylene oxide. The hydrogel polymers have macrophage activity and are useful in wound dressings, as disclosed in U.S. Pat. No. 4,781,921, but are non-adhesive.

H. K. Pokharna et al, *Journal of Bioactive and Compatible Polymers*, 5, 42-52 (1990) describes copolymers of hydroxyethyl methacrylate (HEMA) with "Quadrol" methacrylate and with Various aminoalkyl methacrylamides as substrates for growth of fibroblast cells. The materials tested differed in their capacity to support fibroblast cell growth.

A major limitation of occlusive dressings is that the adhesive layer or adhesive component of a blend, as the case may be, tends to reduce the absorption of fluids in wounds and the moisture transmission rate. Occlusive dressings tend to accumulate wound exudate and may adhere to the wound site.

While desirable characteristics of a material for a wound dressing and other biomedical applications which is both adhesive, hydrophilic and capable of absorbing fluids have been identified in the literature, such characteristics have not been fully achieved in practice. There exists a need for a material which combines all of these characteristics.

DISCLOSURE OF THE INVENTION

This invention provides novel non-toxic, hydrophilic pressure sensitive adhesive hydrogels which are suitable for use in wound dressings and other biomedical appli- cations. These novel hydrogel compositions combine high absorptivity for fluids with good adhesiveness to non-wounded skin and ready removability from a wound.

The hydrogel compositions of this invention are crosslinked polymers having repeating units of at least one of the following formulas (III), (XIII), (XIV) OR (XVII):

and blends of such polymers. The equilibrium water content of these hydrogel polymers is generally about 85% to about 95% by weight of water.

This invention further provides oligomers, i.e., or non-crosslinked polymers of low molecular weight (typically about 1700-5000) and having the repeating units of at least one of the aforesaid formulas (III), (XIII), (XIV) and (XVII).

The non-crosslinked polymers or oligomers are made according to this invention by reacting a disubstituted aliphatic diamine of the following formula (I)

$$R_1N—(CH_2)_y—NR_2 \quad (I)$$

or the following formula (XI)

or the following formula (XVI)

or two or more such disubstituted aliphatic diamines, with a difunctional alkylating agent or mixture thereof, preferably one or more diepoxides of the following formula (II)

The diepoxide or mixture thereof may be either a diepoxyalkane of diglycidyl ether of a dihydric aliphatic alcohol or combination of the two.

Throughout the specification, including the claims, the above symbols shall have the following meanings:

B is a monovalent blocking group.

$R_1$ and $R_2$ may the same or different (and are preferably the same) and each is an alkyl radical of 1 to about 6 carbon atoms or a hydroxyalkyl radical of 2 to about 6 carbon atoms.

X is an alkylene group or a dioxyalkylene group, i.e., $—(CH_2)_x—$ or $—O(CH_2)_xO—$.

x and y may be the same or different and each is an integer from 2 to about 6.

"n" is from about 4 to about 20.

This invention provides novel wound dressings comprising a hydrogel of the composition described herein on a suitable non-toxic waterproof backing material.

BRIEF DESCRIPTION OF THE DRAWINGS

The sole figure of drawing is a cross-sectional view of a wound dressing in accordance with this invention.

BEST MODE FOR CARRYING OUT THE INVENTION

This invention will now be described in greater detail with reference to various embodiments including the best mode and preferred embodiment of the invention.

The hydrogel polymer compositions of this invention, in general, belong to one of the following series: (1) polymers in which the repeating units have the general formula (III), (2) polymers in which repeating units have the general formula either (XIII), (XIV) or (XVII), (3) mixed polymers having both repeating units of the formula (III) and repeating units of the formula (XIII), (XIV) or (XVII), and (4) blends of two or more of the above polymers.

First Series

Polymers of the first series are prepared from symmetrically disubstituted diamines, i.e., N,N'-disubstituted diamines of the general formula (I) given previously.

Hydroxyalkylated diamines of the formula (I) wherein $R_1$ and $R_2$ are the same and both are hydroxyalkyl can be made by reacting one mol of an aliphatic α,ω-diamine containing from 2 to about 6 carbon atoms with 2 mols of an alkylene oxide (or epoxyalkane) according to the procedures described in Smith et al, J. Polymer Sci. or U.S. Pat. No. 4,781,921, both cited supra. In particular, the preferred starting material of the formula I, i.e., N-N'-bis(2-hydroxypropyl)ethylenediamine (I-a), can be made be reacting one mol of ethylenediamine with 2 mols of propylene oxide according to this process.

Other representative alkylene diamines which can be reacted in the same way are 1,3-diaminopropane, 1,4-diaminobutane, 1,5-diaminopentane, 1,5-diamino-3-methylpentane and 1,6-diaminohexane. These can be represented by the general formula $H_2N(CH_2)_yNH_2$.

The alkylene oxide is a 1,2-epoxyalkane containing from 3 to about 6 carbon atoms. The compound is monofunctional, i.e., it contains one epoxy unit per molecule. It is highly desirable that this epoxy group be at the end of the carbon chain, in the 1.2 position since better results are obtained when the alpha carbon atom of groups $R_1$ and $R_2$ is a —$CH_2$—group with two unsubstituted hydrogen atoms and in which the hydroxyl radical is attached to the beta carbon atom. Representative alkylene oxides, besides propylene oxide, including 1,2-epoxybutane, 1,2-epoxypentane, 1,2-epoxy-3-methylbutane and 1,2-epoxy hexane.

Alkylated diamines of the formula (I) wherein $R_1$ and $R_2$ are the same and both are lower alkyl can be made by reacting one mol of an aliphatic α,ω diamine containing 2 to 6 carbon atoms as above described with a lower alkyl halide, such as methyl chloride, methyl bromide, ethyl chloride, ethyl bromide, n-propyl chloride or bromide, isopropyl chloride or bromide, n-butyl chloride or bromide, isobutyl chloride or bromide, sec-butyl chloride or bromide, tert-butyl chloride or bromide, etc. General procedures for such reaction are known in the art and disclosed in U.S. Pat. No. 4,937,269.

Mixed disubstituted diamines of the formula (I), i.e., those in which $R_1$ and $R_2$ are different, are more difficult to prepare, usually requiring several steps, and as far as is known offer no advantages over disubstituted diamines of the formula (I) in which $R_1$ and $R_2$ are the same. Mixed diamines of formula (I) can be prepared, if desired, according to methods described in U.S. Pat. No. 4,937,269.

The N,N'-disubstituted diamine of the formula (I) is reacted with one or more difunctional alkylating agents in an essentially 1:1 mol ratio to give a non-crosslinked polymer. The alkylating agents generally are aliphatic compounds having from 2 to about 12 carbon atoms and containing two functional atoms or groups which are reactive with the amino hydrogen atoms of the diamine. Preferred alkylating agents are diepoxy compounds of the formula (II). This results in a water-soluble, non-crosslinked polymer having a molecular weight of about 500 to about 50,000 (or higher), preferably about 1000 to about 10,000 and most preferably about 1700 to about 5,000, and having repeating groups of the formula (III) given above. The reaction of (I) with one or more diepoxides (II) follows a typical epoxide ring opening polymerization under slightly basic conditions, in which the disubstituted amine (I) acts as a bifunctional monomer. Polymerization is carried out in an alcohol solution, where the hydroxyl groups catalyze a proton transfer to the oxygen of the epoxide Suitable solvents include lower alkyl alcohols ethanol, methanol, and isopropyl alcohol, or tetrahydrofuran (THF). Reaction is carried out at elevated temperature, (e.g., approximately 60°–100° C.), typically at reflux temperature or only slightly below, and at atmospheric pressure. (All reactions carried out in accordance with this invention may be and preferably are carried out at substantially atmospheric pressure). The reaction takes place at elevated temperature over a period of time, and the polymerization process can be monitored by progressive increase in viscosity. Polymerization is continued until a desired degree of polymerization, e.g., from about 4 to about 20, corresponding to a number average molecular weight from about 1700 to about 5000, is reached. This may be recognized by a solution viscosity of about 500 to 1500 centipoises at reaction temperature when the reaction is carried out in ethanol at 80° C.; the viscosity corresponding to the desired degree of polymerization will vary as the solvent and the temperature are varied. The solvent can be removed in vacuo and the resulting material, which is a highly viscous clear liquid, may be redissolved in a small amount of a suitable solvent such as THF, ether or dioxane and precipitated with ethyl acetate, hexane or other hydrophobic precipitant.

Suitable diepoxy compounds include diepoxy alkanes, such as 1,2,5,6-diepoxyhexane 1,2,7,8-diexpoxyoctane and 1,2,9,10-diepoxydecane; and diglycidyl ethers such as 1,2-ethanediol diglycidyl ether, 1,3-propanediol diglycidyl ether, 1,4-butanediol diglycidyl ether and 1,6 hexanediol diglycidyl ether, and 2,3-dimethyl-1,4-butanediol diglycidyl ether.

One or more diepoxy compounds may be used as reactants. It is particularly desirable to react one mol of a diexpoxyalkane and one mol of a diglycidyl ether with 2 mols of a N,N'-disubstituted diamine.

Other difunctional alkylating agents, as for example one or more aliphatic dihalo compounds, particularly oxygen-containing dihalo compounds, can be used in place of one or more diepoxides if desired. Representative dihalo compounds include, for example, 1,4-dibromobutane, 1,6-dibromohexane, 1,4-dichloro-2,3-butanediol and 1,4-dibromo-2,3-butanediol. 1,3-dichloro-2-propanol 1,3-dibromo-2-propanol, 1,4-dibromo-2-butanone and 1,4-dicholoro-2-butanone. Halo-substituted secondary alcohols and ketones couple with the disubstituted amine (I) through the halogen atoms. Halo-substituted secondary alcohols and ketones and in particular dihydroxy dihalo compounds are desirable alkylating agents because they introduce oxygen into the polymer molecule, imparting a desired degree of hydrophilicity into the end product hydrogel polymer. The diepoxides are preferred, particularly over the non-oxygen containing dihalides, because the diepoxides react readily with the disubstituted diamines under mild conditions and the hydroxy groups introduced into the polymer molecule also impart a desired degree of hydrophilicity into the end product hydrogel polymer.

More than one disubstituted diamine of the formula (I) can be reacted if desired. The proportions of total disubstituted diamine(s) (I) and difunctional alkylating agent(s) should be essentially stoichiometric.

The reaction product of (I) and (II) is a highly hydrophilic, water soluble linear non-crosslinked polymer having repeating groups of the formula (III) given above and having a number average molecular weight from about 500 to about 50,000, preferably about 1000 to about 10,000, particularly from about 1700 to about 5000. The molecular weight can be measured fairly precisely by nuclear magnetic resonance (NMR), which "counts" end groups by analysis, or by gel permeation chromatography (GPC).

Polymers of the first series may be described as polymers in which the repeating groups or units consist essentially of repeating groups or units of the formula (III). By correlating the molecular weight measured in this matter with viscosity, one can use solution viscosity as a means to monitor the process of polymerization while the reaction is taking place.

The non-crosslinked polymer, in addition to having repeating groups (III), has an unreacted secondary amino group at one end of each polymer chain and a unreacted epoxy group at the other end of each chain. One end group E can be represented by the following formula:

(E₁)

and the other end group $E_2$ can be represented by the following formula:

(E₂)

Cross-linking of a non-crosslinked polymer having repeating groups (III) as described above may be carried out by first reacting the unreacted amino hydrogen atoms of the secondary amino end groups with a difunctional alkylating agent if desired, i.e., endcapping (this step is optional but preferred), then cross-linking with an amine cross-linking agent.

Reaction of the unreacted amino hydrogen atoms (i.e., end capping) can be carried out using a diepoxide of the formula II given above, or other diepoxide not having additional reactive groups, or with another difunctional compound, such as a dihydroxy dihalo compound, which has two groups that are reactive with an amino hydrogen atom. The end capping agent may be either the same as or different from the divalent alkylating agent used to react with a diamine of the formula (I). Preferably the end capping agent and the divalent alkylating agent are the same compound.

End capping is optional as noted above; the advantage of end capping is that all active end groups will be the same (e.g., all epoxy groups) in an end capped polymer, so that the polymer will not have the tendency to self-crosslink. Self-crosslinking is acceptable, but the course of cross-linking can be better controlled by end capping and then using an added cross-linking agent, as will be described below.

Use of a diepoxy end capping agent, say a compound of the formula (II), results in an end capped non-crosslinked polymer in which the end groups are epoxy groups. Similarly, use of a dihalo compound as end capping agent results in a non-crosslinked polymer in which the end groups are halogen atoms. The non-crosslinked polymer can be either completely or partially endcapped by choice of the amount of end capping agent used. A partially end capped non-crosslinked polymer will have some secondary amino end groups remaining, but will have less tendency to self-crosslink then an otherwise similar non-crosslinked polymer which is not end capped.

Monofunctional compounds which are reactive with an active hydrogen atom can be used in place of the foregoing difunctional compounds, but, unlike the difunctional compounds, do not furnish additional cross-linking sites. The difunctional compounds are therefore ordinarily preferred.

Reaction of the remaining active amino groups can be carried out at reflux temperature and at atmospheric pressure in a suitable solvent such as methanol, ethanol, isopropyl alcohol, or other lower alkyl alcohol. Reaction takes place in about 2 hours at 80° C. in ethanol. The solvent can be removed in vacuo or by other suitable means. The product is an end capped non-crosslinked polymer that is highly viscous. A functional crosslinked polymer can be attained with either complete or partial endcapping.

Cross-linking can be carried out with an amine cross-linking agent having a functionality of 2 or higher. Usually the crosslinking agent has a functionality greater than 2, e.g., 3 or higher. A preferred cross-linking agent is diethylenetriamine. Other amine cross-linking agents include triethylenetetramine. Amine cross-linking agents are capable of reacting with either epoxy end groups or halogen atoms.

Cross-linking may be carried out in a suitable solvent, e.g., a lower alcohol such as ethanol, methanol or isopropyl alcohol, or THF or ether, at a temperature from about 60° C. o about 80° C. The required time for cross-linking is ordinarily from about 1 to about 3 hours. Progress of the crosslinking can be determined by periodic sampling for extractables. The crosslinking reaction is ordinarily continued until no extractables remain. Enough cross-linking agent is added to effect about 5 to about 15 mol% cross-linking. The mol percentage of cross-linking agent is preferably 8 to about 12 percent, most particularly about 10%. The mol percentage of cross-linking agent is equal to the moles of cross-linking agent divided by the number of mols of polymer, which is taken to be the weight of polymer divided by the number average molecular weight $M_n$. Tackiness or adhesiveness of crosslinked hydrogel polymers decreases as the degree of crosslinking increases, and is undesirably low in polymers which are more than 20 mol percent crosslinked. Polymers which are insufficiently crosslinked (i.e., less than about 5 mol percent) have some extractables, which is undesirable in a wound dressing).

Cross-linked polymers according to this first series of the invention are highly hydrophilic hydrogels, which, although water insoluble, have a high equilibrium water content (EWC) and high water uptake. They adhere readily to dry surfaces but not to wet surfaces. When applied to dry surfaces, these polymers exhibit both initial tack and long term adhesion. In addition, hydrogel polymers of this invention have the capacity to promote human skin cell growth, and this is helpful in the healing process.

Equilibrium water content of hydrogel polymers of this first series is from about 85% to about 93% by weight. This percentage by weight is based on total hydrated polymer weight, and is equal to the difference between hydrated and dry polymer weights, divided by dry polymer weight and multiplied by 100. Equilibrium water content can be determined by soaking the cross-linked polymer in water at ambient temperature for sufficient time to reach equilibrium (24 hours is regarded as sufficient), or by exposing the hydrogel polymer to 100% relative humidity at 25° C. for sufficient time to reach equilibrium (e.g., at least 24 hours). The water uptake is the percent of weight gain upon hydration of initially dry polymer, and is in the range of about 600% to about 1000%. Both of these quantities can be computed as will be described in the examples. When equilibrium water content and percentage uptake are in the above stated ranges, the polymer will have the desired characteristics, including hydrophilicity, for the purposes of this invention. The desired hydrophilicity is characteristically achieved when the oxygen content of the polymer, by elemental analysis, is from about 20% to about 35% by weight. This desired oxygen content is achieved by introducing hydroxyl or other oxygenated groups into the polymer chain, e.g., through use of hydroxyalky substituents $R_1$ and $R_2$ in the starting disubstituted diamine (I), and in use of either diepoxides or hydroxyl-substituted dihalo alkanes as difunctional alkylating agents.

The properties of hydrogels of this invention make them ideal materials for wound dressings. The high degree of water uptake is also manifested when the material is applied to a wound, since these cross-linked polymers take up large volume of liquid wound exudate before the dressing has to be changed. Hydrogels of this invention retain their three-dimensional structure and cohesiveness even when wet. They are clear and colorless. Since these hydrogel polymers adhere readily to dry surfaces but not to wet surfaces, they will adhere readily to undamaged skin adjacent to a wound but do not adhere or stick to the wound. Because of this, a wound dressing having such hydrogel polymer as its active ingredient can be readily removed from a wound without damaging the wound. When it is time to remove a wound dressing of this invention, the non-wounded skin holding the ends of an adhesive wound dressing of this invention can be moistened for ready removal.

Figure 1:
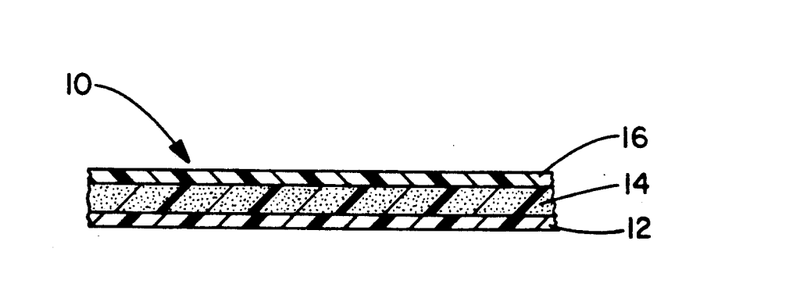

A hydrogel polymer of this invention can form the adhesive layer of a pharmaceutically acceptable composite article which is adhered to the skin of a patient. Such composite articles include, for example, wound dressings, transdermal drug delivery systems, and ostomy devices. Such composite article will be described with particular reference to a composite wound dressing such as that shown in the sole figure of the drawing. Referring to the drawing, 10 is a composite wound dressing according to this invention. The wound dressing 10 comprises a pharmaceutically acceptable backing 12, which is typically and preferably polyurethane, and which is about 1 to 3 mils (about 0.025 to about 0.076 mm) thick. A hydrogel polymer layer 14, made in accordance with this invention, is adhered to one side of the backing material. This hydrogel polymer layer may be from about 1 to about 100 mils (about 0.025 to about 2.5 mm) thick in the dry state. The composite dressing may include (and preferably does include) a release liner 16, which is applied to the outside surface of the gel liner. This release liner may be conventional, and its inside surface has release characteristics which may be achieved in a conventional manner, i.e., by the presence of a suitable silicone compound having release properties.

A composite wound dressing as illustrated in the drawing may be of any convenient form and shape. For example, such wound dressing may be in the form of an adhesive tape of desired width say ½ inch to 3 inches or about 1.27 to 7.6 cm) which is wound around itself on a roll. Alternatively, the wound dressing may be in the form of a patch of desired size and shape, usually either rectangular or circular. Sizes and thicknesses may be the same as those in presently known wound dressings.

A wound dressing of this invention may be applied in a conventional manner. Thus, for example, when the dressing is in the form of a long tape, the ends will be applied to undamaged skin on either side of the wound and the central portion will be over the wound, with the hydrogel layer 14 against the wound and undamaged skin on either side thereof. Similarly, when a composite wound dressing as shown in the drawing is in the form of a circular or rectangular patch, the edges will be adhered to undamaged body tissue surrounding the wound site while the central portion is over the wound site. Wound dressings of this invention are useful for covering wounds of any type for which wound dressings are presently used. The wound dressings of this invention are particularly useful for covering of burns and ulcerated wounds. Ulcerated wounds include, for example, wounds in diabetic patients and decubitus ulcers. Wound dressings of this invention can also be used as a highly absorptive component in an ostomy dressing.

Similarly, a transdermal delivery system for controlled release of medication into a patient via pores in the skin may also be prepared according to this invention. Referring again to the sole figure of the drawing, such delivery system 10 may comprise a thin flexible waterproof backing 12 having on one side thereof a layer 14 of hydrogel polymer according to this invention, to which has been added a medicament which is to be released slowly into the bloodstream of a patient. The amount of concentration of medicatament is such as to achieve the desired release rate.

Hydrogel polymers of this invention can also be used in conjunction with ostomy devices as a replacement of non-permanent adhesives presently in use. For example, an adhesive hydrogel polymer of this invention may be applied to skin around the circumference of a stoma, or around tubing (e.g., a colon tube) used in certain types of ostomies. By way of illustration, U.S. Pat. No. 4,685,990 shows a representative ostomy device which may be adhered via adhesive layer 142 to the skin of a patient surrounding an ostomy. The adhesive hydrogels of this invention may form the adhesive layer 142. U.S. Pat. No. 4,231,369 shows another representative ostomy device, which employs a shaped, gel-like composition as sealing means for attaching the ostomy device to the human body.

This invention will now be described in further detail with reference to the examples which follow.

Preparation of Starting Material

N,N'-bis(2-hydroxylpropyl)ethylenediamine(I-a) is synthesized according to the method of Smith and Patel, *Journal of Polymer Science: Polymer Letters Edition*, 23, 633 (1985) and U.S. Pat. No. 4,781,921 (Example 1) both cited starting with ethylene diamine and propylene oxide.

EXAMPLE 1

Synthesis of Poly Butoxy Entprol (Poly-BE) (III-a)

To 1,4-butanediol diglycidyl ether (II-a) (9.85 g, 0.0487 mol) was added N,N'-bis(2-hydroxypropyl)ethylenediamine (I-a) (8.59 g, 0.0487 mol) in 40 ml ethanol. The reaction mixture was heated to and maintained at 80° C. for 4 hours. The polymerization process was monitored by the progressive increase in viscosity. Ethanol was removed in vacuo and the resulting highly viscous clear liquid was dissolved in 100 ml THF and precipitated in 200 ml ethyl acetate. Precipitation was repeated twice and, after complete removal of solvents, produced 15.47 g, (0.0409 mol, based on repeating unit formula weight) of poly BE in 84% yield. Analysis by NMR and GPC showed the number average molecular weight Mn to be about 1800. The yield of polymer is therefore about 8.6 millimols (mmol).

EXAMPLE 2

Synthesis of Poly Butoxy/Ethylene Entprol: Poly-BEE (III-b)

A 250 ml, round bottom flask, equipped with a magnetic stirring bar and a reflux condenser was charged with N,N'-bis(2-hydroxypropyl)ethylenediamine (I-a) (18.58 g, 0.1054 mol), 1,4-butanediol diglycidyl either (II-a) (10.66 g, 0.0527 mol), 1,2,7,8-diepoxyoctane (II-b) (7.50 g, 0.0527 mol) and 50 ml ethanol. The flask was maintained in a constant temperature oil bath at 80° C. for 6 hrs. Ethanol was removed in vacuo and the purification procedure for poly BE was followed to produce 31.8 g (0.09 mol, based on repeating unit formula weight) of highly viscous clear poly BEE in 87% yield.

EXAMPLE 3

End Capping and Crosslinking of Poly-BE

A 250 ml. round bottom flask, equipped with a magnetic stirring bar and a reflux condenser was charged with poly-BE (15.47g, 8.6 mmol), 1,4-butanediol diglycidyl ether (1.8 g, 9.0 mmol) and 40 mL of ethanol. The flask was maintained at 80 ° C. for 3 hrs. Ethanol was removed in vacuo. The resulting highly viscous end capped product was dissolved in 175 ml THF and precipitate in 300 ml ethyl acetate. The white precipitate was dried in vacuo and dissolved in 35 ml ethanol. Crosslinking was initiated by the addition of diethylenetriamine (0.10 ml, 0.93 mmol). This represents about 10.8 mol percent of cross-linking agent. The temperature was maintained at 80° C. for 1½ hours. The reaction mixture was then concentrated in vacuo. A crosslinked film, approximately 1 mil thick, was obtained by drawing out the hot viscous polymer on Teflon coated metal sheet, using a Gardner knife (Gardner Labs, Inc.). ("Teflon" is a registered trademark of E. I. duPont de Nemours & Co., Wilmington, Del., USA, for polytetrafluoroethylene). One mil thick films were also drawn out on polyurethane film for use in peel adhesion. Poly-BE was cured at room temperature.

EXAMPLE 4

Endcapping and Crosslinking of Poly-BEE

The procedure of example 3 was followed resulting in endcapped and crosslinked poly-BEE.

EXAMPLE 5

Equilibrium Water Content (EWC) and Water Uptake (WU)

Equilibrium water content (EWC) is defined by the following equation:

$$EWC = \frac{\text{Weight of hydrated material} - \text{weight of dry material}}{\text{weight of hydrated material}} \times 100$$

Water uptake is defined by the following equation:

$$\text{Water Uptake} = \frac{\text{wt. of hydrated material} - \text{wt. of dry material}}{\text{weight of dry material}} \times 100$$

Equilibrium water content and water uptake of each polymer material were determined as follows: An accurately weighted amount (approximately 0.35 g) of dry (over dry at 40° C.) polymer is hydrated by soaking in 100 mL of water for 24 hours at room temperature. The hydrated polymer is removed by filtration and the weight of the polymer is obtained.

Water uptake and equilibrium water content are shown in Table 1 below:

TABLE 1

| Compound | Number | % Water Uptake | Equilibrium Water Content |
|---|---|---|---|
| Poly-BE | III-a | 971 | 90.66 |
| Poly-BEE | III-b | 630 | 86.30 |

EXAMPLE 6

Peel adhesion at 180° C. Angle

Peel adhesion of the adhesive strip of Example 3 to dry glass is done according to ASTM standard test method D3330 M-87 using a 5 kilogram load cell and an Instron 1150 series tester. The crosshead rate was adjusted to 20 cm/min. Test adhesive strips, 1"×5" or 2.54 cm×12.7 cm), of adhesive material on polyurethane backing were cut and then adhered to dry glass for 2 hrs. Each sample was prepared in triplicate. The adhesive strips were peeled at a constant rate and at a peel angle of 180°. Peel force and peel energy were then computed for each sample.

Peel force = (no. of units) (weight in kilograms)

$$\text{Peel Energy} = \frac{\text{Peel Force}(1 - \cos\theta)}{\text{Sample Width}}$$

$\theta = 180°$ , Sample Width = 2.54 cm

Results are shown in Table 2. Table 2 also shows peel force and peel energy with several commercially available bandage materials, which are lettered A-E.

TABLE 2

| # | SAMPLE | Adhesive Coating on Polyurethane Backing | PEEL FORCE N | PEEL ENERGY N/cm |
|---|---|---|---|---|
| A | Bioclusive (Johnson & Johnson) | Acrylate Copolymer | 7.38 ± 0.59 | 5.81 ± 0.47 |
| B | 3M Tegaderm (3M) | | 4.90 ± 0.58 | 3.86 ± 0.46 |
| C | Fasson Copolyester | | 9.39 ± 0.59 | 7.61 ± 0.58 |
| D | Semex Polyurethane | | 11.56 ± 0.34 | 9.05 ± 0.32 |
| E | Hy-Tape | Acrylate Copolymer with Zinc-Oxide | 10.71 ± 0.49 | 8.69 ± 0.17 |
| III-a | Poly-BE | Polymer of Example 3 | 12.02 ± 0.10 | 9.49 ± 0.16 |
| III-b | Poly-BEE | Polymer of Example 4 | 13.61 ± 0.15 | 10.70 ± 0.14 |

EXAMPLE 7

The procedure of Example 6 was repeated except that the adhesive strips were adhered to dry human skin. Results are shown in Table 3.

TABLE 3

| # | SAMPLE | Adhesive Coating on Polyurethane Backing | PEEL FORCE N | PEEL ENERGY N/cm |
|---|---|---|---|---|
| A | Bioclusive (Johnson & Johnson) | Acrylate Copolymer | 1.32 ± 0.22 | 1.04 ± 0.08 |

TABLE 3-continued

| # | SAMPLE | Peel Adhesion to Skin Adhesive Coating on Polyurethane Backing | PEEL FORCE N | PEEL ENERGY N/cm |
|---|---|---|---|---|
| B | 3M Tegaderm (3M) | | 1.15 ± 0.16 | 0.93 ± 0.10 |
| C | Fasson Copolyester | | 1.30 ± 0.09 | 1.03 ± 0.07 |
| D | Semex Polyurethane | | 2.64 ± 0.27 | 2.08 ± 0.21 |
| E | Hy-Tape | Acrylate Copolymer with Zinc Oxide | 0.79 ± 0.20 | 0.62 ± 0.16 |
| III-a | Poly-BE | — | 3.45 ± 0.21 | 3.18 ± 0.42 |
| III-b | Poly-BEE | — | 0.97 ± 0.39 | 0.87 ± 0.25 |

The hydrogels (poly-BE and poly-BEE) described above were found not to adhere to wet glass or wet skin. A spot on a test glass was wetted with a drop (0.1 ml) of water and an adhesive strip was applied to the wet glass spot and to dry glass on either side. Adherence to the wet spot was found to be essentially zero.

EXAMPLE 8

Cell Adhesion and Cell Growth (Fibroblast Cells)

General It has been demonstrated that factors such as polymer surface, hydrophilicity or hydrophobicity are important to cell adhesion and cell growth. In this study cross-linked polymers of the poly BE and poly BEE were synthesized as described in examples 1–4 and structures having repeating groups of Formula III show a cationic amine and several hydroxyl groups as hydrophilic components. The hydrophobic component on the above polymers comprises the butyl ether groups and the methylene linkages of the 1,2,7,8-diepoxyoctane monomer.

Media and Buffers. Dulbecco's modified Eagle is Medium (DMEM) is prepared from commercial powder and supplemented with 3.5 g/L sodium bicarbonate. The composition of DMEM is reported in Freshney, R. I., "Culture of Animal Cells; A Manual of Basic Techniques", second edition, 1987, published by Alan R. Liss, Inc., New York, N.Y., ppg. 74 and 75. Trypsin-EDTA solution 0.01% (v/v) is made in minimum essential medium (MEM). A lysis buffer is prepared with 0.1 M potassium phosphate buffer (pH=7) containing 0.5% (v/v) "Triton" X-100. ("Triton" is a registered trademark of Rohm & Haas Co., Philadelphia. Penna., U.S.A., and "Triton" X-100 refers to a commercially available nonionic surface active agent. Phosphate buffered saline (PBS), is available from Fisher Scientific Company in 1× and 10× strengths, the latter being 10 times as concentrated as the former. The composition of 10×PBS (in grams per liter) is as follows:

TABLE 4

| Composition of 10 XPBS | |
|---|---|
| NaCl | 80 g/L |
| KCl | 3.0 g/L |
| Na$_2$HPO$_4$ | 0.73 g/L |
| KH$_2$PO$_4$ | 0.2 g/L |

Cell Culture. The measurement of balb/c 3T3 fibroblast cell growth on poly-BE and poly-BEE is used as a measure of polymer biocompatibility.

Films of poly-BE (Example 3) and poly-BEE (Example 4), approximately 2 mils (0.05 mm) thick (4"×4" or 10.16×10.16 cm), were swelled and washed extensively in 500 ml of 70% ethanol. The swelled polymer gels that were obtained was washed extensively in 10×PBS, pH 7.2, and stored in the same. The polymer gels were cut into 1" (2.54 cm) circles and placed in 24 well coaster plates. The coaster plates were tissue culture plastic trays (24 wells, each well having a volume of approximately 1.5–2mL) obtainable from Corning Glass Works, Corning, N.Y. The polymer was again washed with 1×PBS pH 7.2 and replaced with 1 mL DMEM.

Balb/c 3T3 fibroblasts (American Type Culture Collection, ATCC, CCL63) were maintained and periodically passaged, or harvested, in the manner described in Pokharna et al cited supra. Cell culture and polymer test procedures are also similar to those described in Pokharna. The cells are maintained on a suitable support surface, and are harvested or passaged, using trypsin-EDTA as an aid in separating the cells from the support surface, when required for testing.

Cells were harvested or passaged by trypsin-EDTA treatment, washed in DMEM and then centrifuged. The cells were counted using a hemocytometer and then diluted to 1×10$^4$ cells/mL in a medium containing PBS and antibiotics. One milliliter (1 mL) of cell suspension is placed on each polymer disc. The plates were maintained in an incubator at 37° C., 5% CO$_2$ under humid conditions for 5 days. The medium was replaced with fresh medium on the third day of culture. Cell growth was observed on the third, fourth and fifth days of cell culture, and were counted on the fifth day.

Tissue culture treated plates (TCTP's) were used as positive controls. The TCTP's were the above described 24-well coaster plates or trays with no polymer test discs in the wells, so that the plate surfaces themselves served as the cell support. Cell culture conditions and procedures were the same as those used for polymer testing as described above. TCTP controls showed an abundant and healthy cell growth. The cell number for the TCTP controls were at least twice the cell numbers of the corresponding hydrogel poly-BE and poly-BEE. The positive TCTP controls exhibited confluent growth and hydrogel poly-BE and poly-BEE test specimens exhibited nearly confluent growth. Cell counts in both test specimens and controls are as shown in Table 5 below:

TABLE 5

| Cell Counts | |
|---|---|
| Poly-BE | 80,000 cells |
| Poly-BEE | 80,000 cells |
| TCTP (Control) | 160,000 cells |

EXAMPLE 8A

Cell Growth (epithelial cells)

Materials and Methods:

Growth of cultured SCC-13 epithelial cells, derived from a human squamous cell carcinoma, were grown in a 3:1 mixture of Dulbecco's modified Eagle's Medium and Ham's F12 medium supplemented with 2mM L-glutamine, 5 μg/mL insulin, 10 mM hydrocortisone, gentamicin (10 micrograms per, 10 micrograms per milliliter μg/mL penicillin, 10 micrograms per milliliter (μg/mL) streptomycin and fetal calf serum. This mixture will be referred to below simply as growth medium. Composition of Ham's F12 medium is given in Freshney, "Culture of Animal Cells" "A Manual of Basic Techniques" cited supra, at pages 74-75.

Growth of Cells on Poly-BE or Poly-BEE cel matrix:

The test polymers were poly-BE (example 3, formula III-a) and poly-BEE (Example 4, formula III-b). Circular gel discs, of polymer 4 cm diameter, were preequilibrated by incubation in several changes of growth medium over a period of three (3) days. Confluent cultures of SCC-13 cells growing in a plastic tissue culture treated plate (TCTP) similar to that described in Example 8 were harvested with Hank's balanced salt solution containing 0.025% trypsin and 1 mM EDTA, washed with growth medium and counted. Hank's balanced salt solution is commercially available. 100 000 cells were seeded onto the surface of a polymer disc in 0.1 mL of growth medium (the growth medium is the mixture described above in this example under "Materials and Methods"). Attachment of the cells to the polymer gel was rapid. Within one hour growth medium was added so that the surface of the medium was equal to the depth of the gel. The cells were then allowed to grow for an additional 5 to 10 days incubated at 37° C. under humid conditions at which time the discs were photographed at 40× and 100× magnification using a Nikon Optiphot phase contrast microscope.

Cell growth on TCTP control discs was carried out in the as in the preceding paragraph.

Results: Observed cell growth was the same for both test polymers and controls.

Second Series

Another series of polymers according to this invention are the branched non-crosslinked polymers or oligomers having repeating units of formula (XIII) and cross-linked hydrogel polymers prepared therefrom.

The first step in preparing polymers according to this second embodiment is to react one mol of an alkylene diamine of the general formula $H_2N(CH_2)_yNH_2$ with 2 mols of a blocking agent, thereby to produce an N N-disubstituted diamine of the general formula (XI), The preferred axylene diamine is ethylenediamine. In general, the suitable alkylene diamines are those containing from 2 to about 6 carbon atoms as described above.

The blocking group (B) can be any monovalent radical which is stable during at least one ensuing synthesis step which follows, but which can be removed before synthesis of the desired hydrogel polymer is complete. The blocking group (B) can be a tri(lower alkyl)silyl radical containing from 1 to about 4 carbon atoms, preferably trimethylsilyl. The compound N,N-bis(-trimethylsilyl)ethylenediamine (XI-a) (the preferred compound of formula (XI)) can be prepared according to the method described in West et al, Journal of the American Chemical Society 90 (3), 727-731 (1968). Analogous procedures can be used when starting with a homologous alkylene diamine or a homologous trialkylsilyl blocking agent.

Reaction of the partially blocked alkylene diamine derivative of the formula (XI) with a difunctional alkylating agent such as a diepoxide of the formula (II) or mixture thereof results in a branched chain cross-linked polymer having repeating units of the general formula (XIII)

Repeating groups of non-crosslinked polymers of the second series normally consist essentially of those of the above formula (XIII).

Polymerization may be carried out in bulk. If desired, one may carry out bulk polymerization at the outset and add a solvent as the reaction mixture becomes highly viscous. Polymerization takes place under slightly basic conditions.

The polymer having the repeating units (XIII) has an unreacted epoxy group at one end of each polymer chain and an unreacted secondary amino group at the other end of each polymer chain.

Polymers having the repeating group XIII may be used as intermediates and as polymer silating agents.

The blocking group B can be removed by known means. When the blocking group is trimethylsilyl, removal is effected by heating the polymer in a solution of a lower alcohol, such as methanol or ethanol. This removes the blocking groups B, resulting in a polymer having repeating groups of the general formula (XIV)

Simultaneously cross-linking takes place between a primary amino group ($-NH_2$) on one polymer chain with an epoxide end group on another polymer chain. This results in a crosslinked hydrogel polymer having repeating groups of the formula (XIV). Complete curing of this crosslinked polymer takes place in air at ambient to slightly elevated temperatures (e.g., about 20°-50° C.).

The cross-linked hydrogel polymers of this second general embodiment or series have properties similar to those of the first embodiment.

Equilibrium water content of polymers of the second series is typically from about 85% to about 95% by weight water. Oxygen content, by elemental analysis, is typically from about 20% to about 35% by weight. On the other hand, polymers of this second series, although not cytotoxic, have been observed not to actively support desired cell growth of fibroblasts or epithelial cells at least to the extent that polymers of the first series described above promote such cell growth. Accordingly, the polymers of the first series described previously are regarded as preferable to those of the second series.

Hydrogel polymers of this second general embodiment can be used in composite wound dressings in the same manner as the hydrogel polymers of the first general embodiment. Wound dressings can have the structure shown in the sole figure of the drawing.

According to a variation of the synthesis scheme in this second series of general embodiment, a blocked diamine monomer of the formula (XI) may be reacted with an epoxyalkane such as propylene oxide or other monofunctional alkylating agent such as methyl chloride, in a suitable solvent such as tetrahydrofuran to introduce groups $R_1$ and $R_2$ as described in the first series. ($R_1$ and $R_2$ are preferably the same. When $R_1$ and $R_2$ are different, several steps are usually required, and methods described in U.S. Pat. No. 4,937,269 may be used). This gives a monomer of the general formula XV shown below.

Deblocking can be carried out as described above, e.g., with methanol at elevated temperature to give an N,N-disubstituted diamine of the general formula (XVI) as follows:

The asymmetrically disubstituted diamine (XVI), which has two free amino hydrogen atoms attached to the same nitrogen atom, can be reacted with one or more difunctional alkylating agents, such as a diepoxide of the formula (II) or mixture thereof to produce a branched chain non-crosslinked polymer having repeating units of the general formula (XVII) shown below.

The polymer chains each have a free secondary amino group at one end of the chain and an unreacted epoxy group at the other end of the chain, similar to the polymers of the first series. Cross-linking occurs by reaction of secondary amino groups with epoxy groups, followed by air curing at ambient to slightly elevated temperatures (e.g., about 20°-50° C.).

Crosslinked hydrogel polymers of the second series generally have repeating groups consisting essentially of groups of the formula (XIV) or of the formula (XVII).

EXAMPLE 9

Synthesis of BTMSEDA-BDE Copolymer (XIII-a)

N,N-bis(trimethylsilyl)ethylenediamine was synthesized according to the method of West et al, *J. Am. Chem. Soc.*, 90 (3), 727-731 (Jan. 13, 1968). To 1,4-butanediol diglycidyl ether (10.10 g, 0.05) was added N,N-bis(trimethylsilyl)ethylenediamine (10.20 g, 0.05 mol) and maintained in a constant oil bath at 80° for 4 hours. To the resulting viscous liquid was added 15 ml THF and the resulting mixture was maintained at 80° C. for an additional one hour. The resulting mixture is essentially bis(trimethylsilyl)ethylenediamine-butanediol ether (BTMSEDA-BDE copolymer (XIII-a). Methanol (30 ml) was added and the mixture was stirred at 25° C. for 16 hours and then for an additional 1 hour at 80° C. The resulting mixture was then concentrated by solvent evaporation to yield 14 g of crosslinked polymer (XIV-a) in 70% yield. A crosslinked polymer film 1 mil thick was obtained by drawing out the hot viscous polymer on a Teflon coated metal sheet, using a Gardner knife (Gardner Labs, Inc.). One mil thick films were also drawn on polyurethane films for use in peel adhesion. Complete curing of films takes place at room temperature (25° C.).

EXAMPLE 10

Equilibrium Water Content and Water Uptake

Equilibrium water content (EWC) and water uptake (WU) of the crosslinked polymer of Example 9 (formula XIV-b) were determined as described in Example 5. Results are shown in Table 6 below:

TABLE 6

| EWC and % Water Uptake-Series II | | |
|---|---|---|
| Compound | % Water Uptake | EWC % |
| XIV-a | 1840 | 94.80 |

EXAMPLE 11

Peel adhesion of the crosslinked polymer (XIV-a) of Example 9 to dry glass and dry skin were measured as described in Example 6. Results are as shown in Table 7 shown below.

TABLE 7

| Peel Adhesion-Series II | | | |
|---|---|---|---|
| Compound | Adhesion to: | Peel Force (N) | Peel Energy |
| XIV-a | skin | 1.82 ± 0.19 | 1.43 ± 0.15 |
| XIV-a | glass | 16.90 ± 0.73 | 13.30 ± 0.57 |

Third Series

The third series of hydrogel polymers according to this invention are prepared by reacting one or more N,N'-disubstituted diamines of the formula (I) and one or more N,N-disubstituted diamines of the general formula (XI) with one or more difunctional akylating agents such as one or more diepoxides of the formula (II).

The N,N'-disubstituted diamine (I) and the N,N-disubstituted diamine (XI) may be reacted in any desired molar proportions, but the total amount of diepoxide(s) or other difunctional alkylating agent(s) should always be essentially the stoichiometric quantity required for reaction with all substituted diamine charged, i.e., the sum of (I) and (XI). Thus, if p is the molar quality of diamine (I) and q is the molar quantity of diamine (XI), then (p+q) is the molar quantity of diepoxide or other difunctional alkylating agent. Best results are obtained with about 5 to about 40 mol % of (XI) and conversely about 60 to about 95 mol % of (I).

The reaction product of (I), (XI) and (II) is a non-crosslinked polymer having repeating groups of both the formulas (III) and the formula (XIII) given earlier. In addition, each polymer chain will have end groups similar to end groups $E_1$ and $E_2$ disclosed earlier, i.e., an unreacted secondary amino (or —NH) group (which may be derived from either a compound (I) or a compound (XI)) at one end of the chain and an unreacted epoxy group at the other end of the polymer chain.

The moieties derived from (I) and those derived from (XI) occur in random sequence in the polymer chain. In other words, repeating groups (III) and repeating groups (XIII) occur in random sequence.

Next, the blocking groups B (typically trimethylsilyl) are removed by treatment with a protic solvent such as methanol (preferred) or ethanol, as described in the second series above, leaving free primary amino groups (—NH$_2$). This results in spontaneous cross-linking due to the reaction of primary amino groups from the second series polymer with epoxy groups of the first series polymer, i.e., a primary amino group from one polymer chain with an epoxy group from another polymer chain, in a manner similar to that described above with respect to polymers of second series. Complete curing takes place in air at ambient to slightly elevated temperatures (about 20°-50° C.). The resulting product is water insoluble hydrophilic hydrogel which typically has an equilibrium water content and a water uptake within the ranges discussed above.

The polymers of this third series, like those of the first and second series, adhere readily to dry surfaces including dry skin but not wet surfaces including wet skin. Therefore, these polymers will adhere little if at all to skin at a wound site which is typically moist. Adhesiveness tends to be between the values observed in first series and second series polymers, the values tending to vary with the relative values of p and q. The polymers of the this third series, like those of the first series, also tend to promote cell growth of desired cells and therefore aid in the healing process. Again, the degree of cell growth promotion tends to be between the degrees of cell growth promotion observed in first series and second series polymers, the value varying with the relative values of p and q. An advantage of hydrogel polymers of this third series is that they combine the desirable qualities of the first and second series polymers, i.e., greater adhesiveness as observed in the second series polymers and good cell growth promotion a observed in the first series.

Equilibrium water content of polymers of the third series is from about 85% to about 95% by weight. Oxygen content by elemental analysis is from about 20% to about 35% by weight.

Polymers of third series may constitute the active material layer 14 of a bandage as illustrated in the sole figure of drawing. Further details of such bandage are as described previously.

Synthesis of a specific polymer of the third series (series III) will now be described below for purpose of illustration.

EXAMPLE 12

Synthesis of Polymer of Series III:

N,N'-bis(2-hydroxypropyl)ethylenediamine was synthesized according to the method of Smith & Patel, *Polymer Sci, Polymer Letters Edition*, 23, 633 (1987). (1). N,N-bis-(trimethylsilyl)ethylenediamine was synthesized according to West et al *J. Am. Chem. Soc.* 90 (3) 727-731. A 250 ml reaction flask was charged with N,N'-bis(2-hydroxypropyl)ethylenediamine (I-a) (6.60 g, 0.038 mol) and 1,4-butanedioldigylcidyl ether (ii-a) (10.0 g, 0.05 mol) with 8 ml THF and maintained in a constant oil bath at 80° C. for 2 hours. N,N-bis(trimethylsilyl)ethylenediamine (XI-a) (2.55g, 0.012 mol) was added and stirred for an additional 2 hours at constant temperature A 50/50 mixture of ethanol/methanol (20 mL) was added and the resulting mixture was stirred at 25° C. for a period of 24 hours and then for an additional 1 hour at 80° C. The mixture was concentrated by solvent evaporation to yield 18 g of polymer in a 90% yield. A crosslinked film 1 mil thick was obtained by drawing out the hot viscous polymer on to a Teflon coated metal sheet, using a Gardner knife. Curing of films is complete at 40° C. in about 3 to 4 hours.

Fourth Series

A hydrogel polymer composition according to the fourth series is a blend of a hydrogel polymer of the first series and a hydrogel polymer of the second series in any desired proportions. Typically, such blend will consist essentially of from about 5 to about 95% by weight of first series polymer and conversely about 5 to about 95% by weight of second series polymers. More usually the blend will contain from about 80 to about 60% by weight of first series polymer and conversely from about 20 to about 40% by weight of second series polymer The desirable qualities of each series of polymer are achieved, the degree of adhesiveness and the degree of cell growth promotion depending upon the relative amounts of the first series polymer and the second series polymer in the blend.

Alternatively, non-crosslinked polymers having repeating units of the general formula (III) (first series) and non-crosslinked polymers having repeating units of the general formula (XIII) (second series) may be formed separately and then mixed in a protic solvent such as methanol, ethanol or water. The blocking groups B of the second series polymer can be removed under deblocking conditions as described above. This leaves free primary amino (—NH$_2$) groups as has been described earlier with particular reference to polymers having repeating units of the formula (XIV) (second series). As described above, these primary amino groups can crosslink with epoxide groups, i.e., a primary amino group of one polymer chain having repeating groups of the formula (XIV) crosslinking with the epoxide end group of another polymer chain, which may have either repeating groups III or repeating groups (XIV). In this fashion a mixed cross-linked product having both repeating groups (III) and repeating groups from (XIV) is formed. This product is a water insoluble hydrophilic hydrogel which has good adhesiveness to dry surfaces (including skin) but not to wet surfaces (including wounded skin) as described above.

Equilibrium water content of polymers of the fourth series is from about 85% to about 95% by weight. The percentage of oxygen, by elemental analysis is from about 20% to about 35% by weight

While this invention has been described with reference to specific embodiments including the best mode and preferred embodiment, it shall be understood that these examples are by way of illustration and not limitation.

What is claimed is:

1. A polymer selected from the group consisting of:
   (A) polymers having repeating units of at least one of the following general formulas:

and and
(B) blends of such polymers,
wherein:
B is a monovalent blocking group;
$R_1$ and $R_2$ are the same or different and each is an alkyl radical of 1 to about 4 carbon atoms or a hydroxyalkyl radical of 2 to about 6 carbon atoms;
X is an alkylene group having from 2 to about 6 carbon atoms or a dioxyalkylene group having from 2 to about 6 carbon atoms;
y is a positive integer from 2 to about 6.

2. A polymer according to claim 1, said polymer being non-crosslinked.

3. A polymer according to claim 1, said polymer being crosslinked.

4. A polymer according to claim 3, said polymer being a hydrogel having an equilibrium water content from about 85 to about 95% by weight.

5. A polymer according to claim 1, said polymer having repeating units of the general formula III.

6. A polymer according to claim 5, said polymer being a polymer of N,N'-bis(2-hydroxypropyl)ethylenediamine, 1,4-butanediol diglycidyl ether and optionally also 1,2,7,8-diepoxyoctane.

7. A polymer according to claim 1, said polymer having repeating units of the general formula XIII.

8. A polymer according to claim 7, said polymer being a non-crosslinked polymer of N,N-bis(trimethylsilyl)ethylenediamine, 1,4-butanediol diglycidyl ether and optionally 1,2,7,8-diepoxyoctane.

9. A polymer according to claim 1, said polymer having repeating units of the general formula XIV.

10. A polymer according to claim 9, said polymer being a crosslinked hydrogel polymer of ethylenediamine, 1,4-butanediol diglycidyl ether and optionally 1,2,7,8-diepoxyoctane.

11. A polymer according to claim 1, said polymer having repeating units of the formula (XVII).

12. A polymer according to claim 11, said polymer being a polymer of N,N'-bis(2-hydroxypropyl)ethylenediamine, 1,4-butanediol diglycidyl ether and optionally also 1,2,7,8-diepoxyoctane.

13. A process for preparing a polymer having repeating units selected from the group consisting of:
(1) units of the general formula III or (2) the general formula XIII;

or (3) the general formula XVII or (4) mixtures thereof
wherein B is a monovalent blocking group
$R^1$ and $R^2$ are the same or different and each is an alkyl radical of 1 to about 4 carbon atoms or a hydroxyalkyl radical of 2 to about 4 carbon atoms;
X is an alkylene group having from 2 to about 6 carbon atoms;
y is a positive integer from 2 to about 6,
which comprises reacting (A)
(1) a substituted diamine compound of the following formula I or mixture thereof or (2) a disubstituted diamine of the formula XI or (3) a disubstituted diamine of the formula XVI (XVI)

or (4) a mixture of such disubstituted diamines,
with (B) one or more difunctional alkylating agents containing from 2 to about 12 carbon atoms.

14. A process according to claim 13 wherein said alkylating agents are diepoxides of the formula II.

15. A process according to claim 13 wherein the compound of the formula (I), (XI) or (XVI) is a compound of the formula I and said polymer has repeating units of the general formula III.

16. A process according to claim 15 wherein the compound of the formula I is a N,N'-bis(2-hydroxypropyl)ethylenediamine and the diepoxide compounds of the formula II are 1,4-butanediol diglycidyl ether and optionally 1,2,7,8-diepoxyoctane 17. A process according to claim 13 in the which the disubstituted aliphatic diamine is a compound of the formula (XI) and the polymer has repeating groups of the formula (XIII).

18. A process according to claim 17 wherein said substituted diamine is N,N-bis(trimethylsilyl)ethylenediamine and the diepoxy compounds are 1,4-butanediol diglycidyl ether and optionally also 1,2,7,8-diepoxyoctane.

19. A process according to claim 13 wherein said disubstituted diamine is a compound of the formula (XI) or (XVI) said process further comprising removing said blocking groups B whereupon the resulting free amino groups react with epoxy end groups to form a cross-linked hydrogel polymer.

20. A process according to claim 19 wherein said crosslinked polymer is a hydrogel polymer having an equilibrium water content from about 85% to about 93%.

21. A process according to claim 13 wherein said polymer has repeating units of the general formula (III) said process further including the steps of reacting a polymer having repeating groups of the general formula (III) and having epoxide end groups with an amine cross-linking agent thereby producing a cross-linked polymer having repeating groups of the formula (III).

22. A process according to claim 21 wherein said cross-linked polymer is a hydrogel polymer having an equilibrium water content from about 85% to about 93%.

23. A pharmaceutically acceptable composite article comprising:
   (A) a pharmaceutically acceptable backing, and
   (B) an adhesive hydrophilic hydrogel polymer layer having a composition as specified in claim 1, adhered to one side of said backing.

* * * * *